United States Patent
Terasaka et al.

(10) Patent No.: US 8,278,488 B2
(45) Date of Patent: Oct. 2, 2012

(54) PROCESS FOR PRODUCING NITROGEN-CONTAINING COMPOUNDS

(75) Inventors: Michio Terasaka, Wakayama (JP); Tetsuaki Fukushima, Wakayama (JP); Hideki Taniguchi, Wakayama (JP); Masaharu Jono, Wakayama (JP)

(73) Assignee: Kao Corporation, Tokyo (JP)

( * ) Notice: Subject to any disclaimer, the term of this patent is extended or adjusted under 35 U.S.C. 154(b) by 216 days.

(21) Appl. No.: 12/672,327

(22) PCT Filed: Aug. 7, 2008

(86) PCT No.: PCT/JP2008/064566
§ 371 (c)(1),
(2), (4) Date: Feb. 5, 2010

(87) PCT Pub. No.: WO2009/020244
PCT Pub. Date: Feb. 12, 2009

(65) Prior Publication Data
US 2011/0207964 A1    Aug. 25, 2011

(51) Int. Cl.
*C07C 209/00* (2006.01)
*C07C 291/04* (2006.01)

(52) U.S. Cl. .................... 564/298; 564/488

(58) Field of Classification Search ............ 564/298, 564/488
See application file for complete search history.

(56) References Cited

U.S. PATENT DOCUMENTS

| | | | |
|---|---|---|---|
| 3,558,710 A | 1/1971 | Stalioraitis et al. |
| 2006/0287556 A1 | 12/2006 | Loenders et al. |
| 2007/0191642 A1 | 8/2007 | Loenders et al. |
| 2009/0292145 A1 | 11/2009 | Fukushima et al. |

FOREIGN PATENT DOCUMENTS

| | | |
|---|---|---|
| GB | 1 235 740 | 6/1971 |
| JP | 2001302596 | * 10/2001 |

OTHER PUBLICATIONS

Nagata, Y. et al., "Reduction With Trichlorosilane V. Tertiary Amines From N, N-Disubstituted amides", Chemistry Letters, Chemical Society of Japan, pp. 989-990 (Jan. 1, 1972) XP 000864430.

* cited by examiner

*Primary Examiner* — Peter G O Sullivan
(74) *Attorney, Agent, or Firm* — Oblon, Spivak, McClelland, Maier & Neustadt, L.L.P.

(57) ABSTRACT

The present invention relates to a process for producing a tertiary amine in the presence of a catalyst containing copper and at least one element selected from the group consisting of elements belonging to Groups 2, 3, 7 and 12 of the Periodic Table (long form of the periodic table), said process including the steps of (a) reducing an amide compound in a hydrogen atmosphere; and (b) introducing a dialkyl amine containing a linear or branched alkyl group having 1 to 6 carbon atoms into a reaction product obtained in the step (a), and treating the reaction product with the dialkyl amine. The present invention provides a process for producing high-purity aliphatic tertiary amines containing a less amount of by-products by reducing aliphatic acid amides under moderate conditions using a chromium-free catalyst, as well as a process for producing amine derivatives such as amine oxide by using the aliphatic tertiary amines, with a good productivity in an economical manner.

22 Claims, No Drawings

PROCESS FOR PRODUCING NITROGEN-CONTAINING COMPOUNDS

CROSS REFERENCES TO RELATED APPLICATIONS

This application is a 371 of International Patent Application No. PCT/JP2008/064566, filed on Aug. 7, 2008, and claims priority to Japanese Patent Application No. 2007-208408, filed on Aug. 9, 2007.

FIELD OF THE INVENTION

The present invention relates to a process for producing nitrogen-containing compounds, and more particularly to a process for producing high-purity aliphatic tertiary amines from aliphatic acid amides, as well as a process for producing amine derivatives.

BACKGROUND OF THE INVENTION

Aliphatic tertiary amines are important intermediate products in domestic and industrial application fields, and have been used in extensive applications such as, for example, fabric softeners, antistatic agents, additives for gasoline, shampoos, rinses, bactericides and detergents.

As the method for producing the aliphatic tertiary amines, there is known an amide reduction method in which an amide obtained from inexpensive regenerative fatty acids is used as a raw material. As the amide reduction method, there are conventionally known various methods using a cobalt-based catalyst, a noble metal-based catalyst, etc. However, any of these conventional methods inevitably require use of a solvent, resulting in problems such as poor productivity.

There is also known the method using a copper/chromium-based catalyst. For example, JP 3-500300A discloses a process for producing tertiary amines in which hydrogen and dimethylamine are flowed through and reacted with a raw amide under a pressure of from 1 to 10 MPa in a batch reactor charged with a copper/chromium/manganese catalyst. US 2006-287556A discloses a process for producing amines in which the reaction is conducted in the presence of hydrogen and an optional amine source under a pressure of from 0.2 to 5 MPa in a fixed bed reactor charged with a hydrogenation catalyst such as a copper/chromium catalyst. However, these catalysts used in the above conventional processes must be handled with great care to ensure a safety, etc., upon disposal. Therefore, there is a demand for chromium-free catalysts. Further, in these methods in which the amide compounds are reduced by flowing a mixed gas of hydrogen and the amine source (dimethylamine) therethrough, there are still present problems to be improved, such as a poor selectivity to the aimed tertiary amines in the method described in JP 3-500300A, and need of flowing a large excess amount of hydrogen through the raw amide in the method described in US 2006-287556A.

There is also disclosed a process for producing tertiary amines in which an amide compound is reduced in a hydrogen atmosphere using a chromium-free copper-based catalyst such as a copper/zinc catalyst, a copper/zinc/ruthenium catalyst and a copper/nickel/ruthenium catalyst (refer to JP 2001-302596A). However, the process is still unsatisfactory because of occurrence of a large amount of by-products such as alcohols.

SUMMARY OF THE INVENTION

The present invention relates to a process for producing a tertiary amine represented by the following general formula (2);

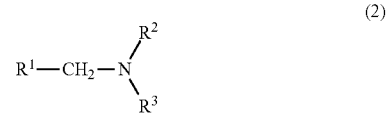

wherein $R^1$ is a linear or branched aliphatic hydrocarbon group having 5 to 23 carbon atoms; and $R^2$ and $R^3$ are respectively a linear or branched alkyl group having 1 to 6 carbon atoms and may be the same or different,
in the presence of a catalyst containing copper and at least one element selected from the group consisting of elements belonging to Groups 2, 3, 7 and 12 of the Periodic Table (long form of the periodic table), said process including the steps of;

(a) reducing an amide compound represented by the following general formula (1), and treating the reaction product with the dialkyl amine

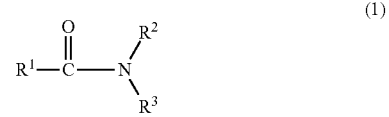

wherein $R^1$, $R^2$ and $R^3$ are the same as defined above,
in a hydrogen atmosphere; and (b) introducing a dialkyl amine containing a linear or branched alkyl group having 1 to 6 carbon atoms into a reaction product obtained in the step (a), and treating the reaction product with the dialkyl amine.

DETAILED DESCRIPTION OF THE INVENTION

The present invention provides a process for producing high-purity aliphatic tertiary amines containing a less amount of by-products by reducing aliphatic acid amides under moderate conditions using a chromium-free copper-based catalyst, as well as a process for producing amine derivatives such as amine oxide from the aliphatic tertiary amines, with a good productivity in an economical manner.

In the process for producing a tertiary amine according to the present invention which includes the steps of (a) reducing an amide compound represented by the above general formula (1) in a hydrogen atmosphere; and (b) introducing a dialkyl amine containing a linear or branched alkyl group having 1 to 6 carbon atoms into a reaction product obtained in the step (a) and treating the reaction product with the dialkyl amine, the tertiary amine represented by the above general formula (2) is produced in the presence of a catalyst containing copper and at least one element selected from the group consisting of elements belonging to Groups 2, 3, 7 and 12 of the Periodic Table (long form of the periodic table).

In the above general formulae (1) and (2), $R^1$ represents a linear or branched aliphatic hydrocarbon group having 5 to 23 carbon atoms. Meanwhile, the branched aliphatic hydrocarbon group also includes an alicyclic group. In addition, the aliphatic hydrocarbon group may be either saturated or unsaturated.

$R^1$ is preferably a linear or branched alkyl group or alkenyl group having 5 to 21 carbon atoms and more preferably 7 to 21 carbon atoms, from the viewpoint of usefulness of the resultant tertiary amine. Specific examples of the alkyl or alkenyl group as $R^1$ include various heptyl groups, various octyl groups, various nonyl groups, various decyl groups, various undecyl groups, various dodecyl groups, various tridecyl groups, various tetradecyl groups, various pentadecyl groups, various hexadecyl groups, various heptadecyl groups, various octadecyl groups, various nonadecyl groups, various eicosanyl groups, various heneicosanyl groups, various tricosanyl groups, various heptenyl groups, various octenyl groups, various nonenyl groups, various decenyl groups, various undecenyl groups, various dodecenyl groups, various tridecenyl groups, various tetradecenyl groups, various pentadecenyl groups, various hexadecenyl groups, various heptadecenyl groups, various octadecenyl groups, various nonadecenyl groups, various icosenyl groups, various heneicosenyl groups and various behenyl groups. Among these groups, preferred are various heptyl groups, various nonyl groups, various undecyl groups, various tridecyl groups, various pentadecyl groups, various heptadecyl groups, various nonadecyl groups, various heneicosanyl groups, various heptenyl groups, various nonenyl groups, various undecenyl groups, various tridecenyl groups, various pentadecenyl groups, various heptadecenyl groups, various nonadecenyl groups and various heneicosenyl groups. The term "various" used herein means all of those groups having a linear chain or a branched chain.

In each of the above general formulae (1) and (2), $R^2$ and $R^3$ are each independently a linear or branched alkyl group having 1 to 6 carbon atoms. Meanwhile, the "branched alkyl group" also includes a cycloalkyl group. Examples of $R^2$ and $R^3$ respectively include methyl, ethyl, n-propyl, isopropyl, n-butyl, isobutyl, sec-butyl, tert-butyl, various pentyl groups, various hexyl groups, cyclopentyl and cyclohexyl. Among these groups, preferred are methyl, ethyl and propyl from the viewpoint of usefulness of the resultant tertiary amine. $R^2$ and $R^3$ may be the same or different.

Examples of the amide compound represented by the above general formula (1) include N,N-dimethyl aliphatic acid amides such as N,N-dimethyl caprylamide, N,N-dimethyl 2-ethylhexane amide, N,N-dimethyl caprinamide, N,N-dimethyl lauroyl amide, N,N-dimethyl myristoyl amide, N,N-dimethyl palmitoyl amide, N,N-dimethyl stearoyl amide, N,N-dimethyl isostearoyl amide, N,N-dimethyl oleyl amide and N,N-dimethyl behenyl amide; and compound obtained by replacing the N,N-dimethyl moiety of these aliphatic acid amides with N,N-diethyl, N,N-dipropyl, N-ethyl-N-methyl, N-methyl-N-propyl or N-ethyl-N-propyl.

On the other hand, examples of the tertiary amine represented by the above general formula (2) include amine compounds corresponding to the above exemplified amide compounds of the general formula (1). Specific examples of the tertiary amine include N,N-dimethyl aliphatic amines such as N,N-dimethyl octyl amine, N,N-dimethyl 2-ethylhexyl amine, N,N-dimethyl decyl amine, N,N-dimethyl lauryl amine, N,N-dimethyl myristyl amine, N,N-dimethyl hexadecyl amine, N,N-dimethyl stearyl amine, N,N-dimethyl isostearyl amine, N,N-dimethyl oleyl amine and N,N-dimethyl behenyl amine; and compound obtained by replacing the N,N-dimethyl moiety of these aliphatic amines with N,N-diethyl, N,N-dipropyl, N-methyl-N-propyl, N-ethyl-N-methyl, N-methyl-N-propyl or N-ethyl-N-propyl.

The catalyst used in the present invention contains (A) copper and (B) at least one element selected from the group consisting of elements belonging to Groups 2, 3, 7 and 12 of the Periodic Table (long-form of the periodic table), and preferably contains, in addition to the components (A) and (B), (C) at least one element selected from the group consisting of platinum-group elements from the viewpoint of a good activity of the resultant catalyst.

Examples of the elements belonging to Groups 2, 3, 7 and 12 of the Periodic Table as the component (B) include magnesium, calcium, barium, scandium, yttrium, lanthanum, cerium, manganese, rhenium, zinc and cadmium. Among these elements, from the viewpoints of good activity and selectivity of the catalyst which are satisfactory in both the reactions of the steps (a) and (b), preferred is at least one element selected from the group consisting of magnesium, calcium, barium, manganese, zinc and yttrium, and more preferred is at least one element selected from the group consisting of magnesium, zinc and barium.

The component (B) may be of any configuration capable of exhibiting a catalytic performance as aimed by the present invention owing to interaction with the component (A) and optionally with the component (C). For example, in the case of a supported catalyst, the component (B) may be selectively supported on a surface of a carrier and/or incorporated into the carrier.

In addition, as the at least one element selected from the group consisting of platinum-group elements, from the viewpoint of a good activity of the resultant catalyst, preferred is at least one element selected from the group consisting of ruthenium, rhodium, palladium, osmium, iridium and platinum, and more preferred is at least one element selected from the group consisting of ruthenium, rhodium, palladium and platinum.

From the viewpoints of good activity and selectivity of the catalyst which are satisfactory in both the reactions of the steps (a) and (b), examples of the preferred configuration of the catalyst include Cu/Mg-based catalysts, Cu/Zn-based catalysts, Cu/Ba-based catalysts, Cu/Mn-based catalysts, Cu/Ca-based catalysts, Cu/Y-based catalysts, Cu/Mn/Ru-based catalysts, Cu/Zn/Ru-based catalysts, Cu/Mg/Pd-based catalysts, Cu/Mg/Rh-based catalysts, Cu/Ca/Pt-based catalysts, etc.

In the catalyst used in the present invention, the content of copper as the component (A) is preferably from 5 to 70% by mass, more preferably from 10 to 60% by mass and still more preferably from 15 to 55% by mass from the viewpoints of good activity and selectivity of the catalyst which are satisfactory in both the reactions of the steps (a) and (b). The mass ratio of the component (B) to the component (A) [component (B)/component (A)] is preferably from 0.001 to 20, more preferably from 0.01 to 5 and still more preferably from 0.05 to 2 from the viewpoint of a good activity of the resultant catalyst. Further, when the catalyst contains the component (C), the mass ratio of the component (C) to the component (A) [component (C)/component (A)] is preferably from 0.0001 to 0.1, more preferably from 0.0005 to 0.05 and still more preferably from 0.001 to 0.01 from the viewpoint of a good activity of the resultant catalyst.

In the present invention, by using such a composite metal-based catalyst, a high catalytic performance which has never been expected by catalysts made of a single metal substance can be achieved.

The contents of the respective metal elements except for platinum-group elements may be quantitatively determined using a wavelength dispersive fluorescent X-ray analyzer. More specifically, 5 g of lithium tetraborate and a stripping agent ($LiCO_3$:$LiBr$:$LiNO_3$=5:1:5) are added to 0.1 g of a sample containing the respective metal elements, and the resultant mixture is fused with an alkali at 1050° C. to prepare glass beads thereof. The thus prepared glass beads are evaluated using a wavelength dispersive fluorescent X-ray analyzer "ZSX100e" available from Rigaku Corporation. The measured X-ray intensity values of the respective metal elements in the sample are compared with those in a calibration curve prepared by mixing the high-purity metal elements at aimed concentrations, thereby determining the contents of the respective metal element in the sample.

On the other hand, the contents of the platinum-group elements in the catalyst is determined as follows. That is, 0.5 g of a sample is charged together with ammonium hydrogensulfate in an amount several ten times the amount of the sample, into a testing tube made of a hard glass, and decomposed under heating. Then, the resultant decomposed product is dissolved in water under heating, and the obtained solution is subjected to ICP emission spectrometry to measure the content of the platinum-group elements in the solution.

In the catalyst used in the present invention, the composite metal may be supported on a carrier. Examples of the carrier include silica, alumina, silica-alumina, zirconia, activated carbon, zeolite, diatomaceous earth, and/or magnesium-containing metal oxides (for example, magnesia, magnesia-alumina, magnesia-silica, hydrotalcite, etc.). Among these carriers, from the viewpoints of good activity and selectivity of the catalyst which are satisfactory in both the reactions of the steps (a) and (b), preferred are silica, alumina, zeolite, diatomaceous earth and magnesium-containing metal oxides, and more preferred are zeolite, silica, alumina and magnesium-containing metal oxides. These carriers may be used singly or in combination of any two or more thereof. The method of supporting the catalyst on the carrier is not particularly limited, and may be appropriately selected from conventionally known methods such as an impregnation method, a precipitation method, an ion-exchange method, a co-precipitation method and a kneading method, depending upon kind of the carrier used.

The catalyst used in the present invention may be produced, for example, by the following method.

That is, an aqueous solution containing nitrates, sulfates, carbonates, chlorides, amine complexes, etc., of the respective metal elements is mixed with an alkali agent such as sodium hydroxide and sodium carbonate and further optionally with a carrier to prepare a precipitate, and the thus prepared precipitate is subjected to solid-liquid separation by a suitable method such as filtration and centrifugal separation. Next, the obtained solid is washed with ion-exchanged water, dried and then calcined at a temperature of preferably from 300 to 1000° C. and more preferably from 400 to 800° C., thereby producing the aimed catalyst in the form of a metal oxide.

The process for producing the tertiary amine according to the present invention is carried out in the presence of the thus produced catalyst, and includes the steps of (a) reducing the amide compound represented by the general formula (1) in a hydrogen atmosphere; and (b) introducing a dialkyl amine containing a linear or branched alkyl group having 1 to 6 carbon atoms into the reaction product obtained in the step (a), and treating the reaction product with the dialkyl amine. In the followings, the steps (a) and (b) are explained.

Step (a)

In the step (a), the amide represented by the general formula (1) is hydrogenation-reduced in the presence of the above-prepared catalyst.

The hydrogenation-reduction reaction may be carried out in a hydrogen atmosphere under normal pressures or under a hydrogen-applied pressure, or in a flowing hydrogen under normal pressures or under applied pressure. The reaction method may be either a continuous method or a batch method. In the batch method, the amount of the catalyst used is preferably from 0.01 to 20% by mass, more preferably from 0.1 to 15% by mass, still more preferably from 0.5 to 10% by mass, further still more preferably from 1 to 10% by mass, and further still more preferably from 3 to 10% by mass on the basis of the amide compound represented by the general formula (1) from the viewpoints of a good reactivity, a good selectivity and low production costs. The catalyst used in the present invention may be recovered after completion of the reaction in the step (b) and then reused from the viewpoint of reducing the production costs.

The reaction temperature is usually from about 140 to about 300° C., preferably from 160 to 280° C. and still more preferably from 180 to 270° C. from the viewpoints of enhancing the reaction rate and suppressing production of by-products. The amount of hydrogen flowed through the reaction system is preferably from 0.1 to 15 mol/h, more preferably from 0.3 to 10 mol/h and still more preferably from 0.5 to 5 mol/h per 1 mol of the amide compound represented by the general formula (1) from the viewpoints of attaining a good reactivity, suppressing production of by-products and facilitating removal of water produced. The reaction pressure is usually from normal pressures to about 25 MPaG ("G" in the unit represents a gauge pressure), preferably from 0.1 to 10 MPaG and more preferably from 0.1 to 5 MPaG from the viewpoints of enhancing the reaction rate and suppressing increase in burden of facilities.

The hydrogenation-reduction reaction is preferably carried out while removing water produced by the reaction from the viewpoint of promoting the reaction. As the method of removing water produced by the reaction, there may be used any of ordinarily used dehydration methods such as method of purging the water out of the reaction system with the above flowing hydrogen or with a flowing mixed gas composed of hydrogen and an inert gas, an azeotropic method, etc. Thus, when hydrogenation-reducing the amide represented by the general formula (1) under the moderate conditions and then subjecting the obtained reaction product to the step (b), the tertiary amine represented by the general formula (2) which contains a less amount of by-products and has a high purity can be produced with a good productivity in an economical manner.

Step (b)

In the step (b), a dialkyl amine containing a linear or branched alkyl group having 1 to 6 carbon atoms is further introduced into the reaction product obtained in the step (a), and treating the reaction product with the dialkyl amine. Incidentally, in the step (a), alcohols are by-produced together with the tertiary amine as an aimed product. These alcohols have a boiling point close to that of the aimed tertiary amine, and are therefore hardly separated from the tertiary amine by distillation, etc. For this reason, in the step (b), in order to further increase a purity of the tertiary amine, the dialkyl amine containing a linear or branched alkyl group having 1 to 6 carbon atoms is introduced to the reaction product to thereby convert the alcohols into dialkyl tertiary amines. The transfer of the step (a) to the step (b) is preferably conducted when the amount of the raw amide compound used in the step (a) is reduced to 5% by mass or less and more preferably when reduced to 1% by mass or less as measured by gas chromatography, from the viewpoints of a good productivity and a less production of the by-products.

Examples of the linear or branched alkyl group having 1 to 6 carbon atoms which is contained in the dialkyl amine used in the step (b) include those alkyl groups respectively exemplified as $R^2$ and $R^3$ of the general formula (1) or (2). Among these alkyl groups, from the viewpoint of usefulness of the resultant tertiary amine, preferred are methyl, ethyl and propyl.

The treatment of the step (b) may be carried out in a hydrogen atmosphere under normal pressures or under hydrogen-applied pressure, or in a flowing hydrogen under normal pressures or under applied pressure. The flowing amount of the dialkyl amine is preferably from 0.001 to 1 mol/h, more preferably from 0.005 to 0.5 mol/h and still more preferably from 0.01 to 0.3 mol/h per 1 mol of the raw amide compound from the viewpoints of a good reactivity and a less production of the by-products.

The treating temperature of the step (b) is preferably from 140 to 270° C., more preferably from 160 to 260° C. and still more preferably from 180 to 250° C. from the viewpoints of a good reactivity and a less production of the by-products. Also, the flowing amount of hydrogen in the step (b) is preferably from 0.1 to 15 mol/h, more preferably from 0.3 to 10 mol/h and still more preferably from 0.5 to 5 mol/h per 1 mol of the raw amide compound from the viewpoints of a good reactivity, a less production of the by-products and facilitated removal of water produced by the reaction. The treating pressure of the step (b) is preferably from normal pressures to 15 MPaG, more preferably from normal pressures to 5 MPaG and still more preferably from normal pressures to 3 MPaG from the viewpoints of enhancing the reaction rate and suppressing increase in load of facilities.

With the provision of the above step (b), since the suitable reaction conditions which are different from those of the step (a) can be selected therefore, the purity of the tertiary amine obtained in the step (a) by hydrogenation-reducing the aliphatic acid amide under the moderate conditions can be further increased. As a result, the aliphatic tertiary amine containing a less amount of the by-products and having a higher purity can be produced with a good productivity in an economical manner.

In the present invention, there are also provided a process for producing amine derivatives by using the tertiary amine produced according to the above production process, in particular, a process for producing amine oxide.

In the process for producing amine oxide, the tertiary amine obtained by the above production process is used as a raw material and reacted with hydrogen peroxide.

In the present invention, as the hydrogen peroxide to be reacted with the tertiary amine, there may be used industrially available aqueous solutions containing hydrogen peroxide in an amount of from 20 to 90% by mass. Although any of the aqueous solutions containing hydrogen peroxide within the above-specified concentration range may be used in the present invention, the concentration of hydrogen peroxide in the aqueous solutions is preferably from 35 to 65% by mass from the viewpoint of a good safety and a good availability. The amount of hydrogen peroxide used is preferably from 0.9 to 1.2 mol, more preferably from 0.95 to 1.1 mol and still more preferably from 1.0 to 1.05 mol per 1 mol of the tertiary amine from the viewpoint of suppressing residual unreacted amine.

The temperature used upon the reaction between the tertiary amine and hydrogen peroxide is preferably from 20 to 100° C., more preferably from 30 to 95° C. and still more preferably from 40 to 90° C. from the viewpoint of suppressing decomposition of hydrogen peroxide. The reaction between the tertiary amine and hydrogen peroxide may be conducted in the presence of a known catalyst to promote the reaction. Examples of the catalyst used in the above reaction include carbon dioxide; a mixture of sodium bicarbonate and sodium pyrophosphate; citric acid, tartaric acid and salts thereof, and phosphotungstic acid and salts thereof.

Further, the reaction between the tertiary amine and hydrogen peroxide may be conducted in a solvent. Water may be usually used as the solvent. However, in order to well control the viscosity of the aqueous amine oxide solution, water may also be used in combination with a water-soluble solvent such as methanol, ethanol and isopropanol.

In the process for producing the tertiary amine according to the present invention, it is possible to produce the tertiary amine with a high reactivity. Further, by using the thus produced tertiary amine as a raw material, it is possible to produce amine oxide therefrom at low production costs. Thus, the tertiary amine produced by the process of the present invention is suitably used for producing amine derivatives such as amine oxide. The amine oxide has been used as an auxiliary activator for various detergents, for example, suitably used in extensive applications such as cleaning agents for tableware, shampoos and detergents for clothes.

Examples of the amine derivatives other than amine oxide which are produced from the tertiary amine obtained according to the present invention include benzalkonium chloride, alkyl trimethyl ammonium salts and alkyl trimethyl acetates. These compounds may be produced by any suitable known methods.

In accordance with the process of the present invention in which the aliphatic acid amide is subjected to hydrogenation-reduction reaction under the moderate conditions and then the obtained reaction product is treated with the dialkyl amine, the amount of hydrogen used therein can be reduced, so that it is possible to produce the high-purity aliphatic tertiary amine containing a less amount of by-products, as well as produce amine derivatives such as amine oxide from the aliphatic tertiary amine, with a good productivity in an economical manner. In addition, since the catalyst used in the process is a chromium-free catalyst, the disposal treatment for the used catalyst can be carried out with a high safety.

In the process for producing the tertiary amine according to the present invention, the high-purity aliphatic tertiary amine containing a less amount of by-products can be produced. The aliphatic tertiary amine produced according to the process of the present invention is an important intermediate product in domestic and industrial application fields, and can be used in extensive applications such as, for example, fabric softeners, antistatic agents, additives for gasoline, shampoos, rinses, bactericides and detergents.

The present invention is described in more detail by referring to the following examples, etc. However, it should be noted that these examples are only illustrative and not intended to limit the invention thereto.

Production Example 1

A separable flask was charged with 100 g of copper nitrate trihydrate and 69 g of magnesium nitrate hexahydrate. The contents of the flask were dissolved in 2 L of ion-exchanged water, and then heated to 50° C. while stirring. The resultant solution was mixed with 33 g of synthesized hydrotalcite represented by the chemical formula: $Mg_{4.5}Al_{12}(OH)_{13}CO_3 \cdot 3.5H_2O$ ("KYOWARD 1000" available from Kyowa Chemical Industry, Co., Ltd.), and heated to 90° C. After dropping an aqueous sodium carbonate solution to the above obtained solution to control a pH value thereof to 7, the resultant mixed solution was aged for 1 h. The thus obtained suspended solution was cooled and then filtered and washed with water, and further dried at 110° C. over a whole day and night. The obtained dried product was calcined at 600° C. under an air flow for 1 h, thereby obtaining a catalyst in the form of a metal oxide. As a result, it was confirmed that the mass ratio of magnesium to copper (magnesium/copper) in the thus obtained metal oxide was 0.43, and the content of copper in the catalyst was 37% by mass.

Production Example 2

The same procedure as in Production Example 1 was repeated except that the amount of magnesium nitrate hexahydrate charged was changed to 34.5 g, thereby obtaining a catalyst in the form of a metal oxide. As a result, it was confirmed that the mass ratio of magnesium to copper (magnesium/copper) in the thus obtained metal oxide was 0.30, and the content of copper in the catalyst was 37% by mass.

Production Example 3

The same procedure as in Production Example 1 was repeated except that 0.17 g of chloro-platinic acid hexahydrate was used in place of 69 g of magnesium nitrate hexahydrate, and the calcination treatment was carried out at 450° C. under an air flow for 3 h, thereby obtaining a supported copper-platinum catalyst. As a result, it was confirmed that the mass ratio of magnesium to copper (magnesium/copper) in the obtained catalyst was 0.18, the mass ratio of platinum to copper (platinum/copper) in the catalyst was 0.0024, and the content of copper in the catalyst was 40% by mass.

Production Example 4

The same procedure as in Production Example 1 was repeated except that 33 g of magnesium oxide (available from Kishida Chemical Co., Ltd.) was used in place of 33 g of the synthesized hydrotalcite, and 12.4 g of barium nitrate was used in place of 69 g of magnesium nitrate hexahydrate, thereby obtaining a catalyst in the form of a metal oxide. As a result, it was confirmed that the thus obtained metal oxide was a supported copper-barium catalyst in which the mass ratio of a sum of magnesium and barium to copper [(magnesium+barium)/copper] in the obtained metal oxide was 1.01, and the content of copper in the catalyst was 36% by mass.

Production Example 5

A separable flask was charged with 100 g of copper nitrate trihydrate and 34 g of manganese nitrate hexahydrate. The contents of the flask were dissolved in 2 L of ion-exchanged water, and then heated while stirring. The flask was further charged at 50° C. with 33 g of synthesized zeolite ("ZEOLUM F-9" available from Tosoh Corporation.), and the contents of the flask were heated to 90° C. After dropping an aqueous sodium carbonate solution to the above obtained solution over 1 h to control a pH value thereof to 7, the resultant mixed solution was aged for 1 h. The thus obtained suspended solution was cooled and then filtered and washed with water, and further dried at 110° C. over a whole day and night. The obtained dried product was calcined at 600° C. under an air flow for 1 h, thereby obtaining a catalyst in the form of a metal oxide. As a result, it was confirmed that the thus obtained metal oxide was a supported copper-manganese catalyst in which the mass ratio of manganese to copper (manganese/copper) in the metal oxide was 0.25, and the content of copper in the catalyst was 35% by mass.

Production Example 6

The same procedure as in Production Example 5 was repeated except that 30 g of zinc nitrate was used in place of 34 g of manganese nitrate hexahydrate, and 0.15 g of ruthenium chloride was further added to the reaction system, thereby obtaining a catalyst in the form of a metal oxide. As a result, it was confirmed that the obtained metal oxide was a supported copper-zinc-ruthenium catalyst in which the mass ratio of zinc to copper (zinc/copper) in the metal oxide was 0.25, the mass ratio of ruthenium to copper (ruthenium/copper) in the metal oxide was 0.0025, and the content of copper in the catalyst was 36% by mass.

Production Example 7

The same procedure as in Production Example 6 was repeated except that no ruthenium chloride was added, thereby obtaining a catalyst in the form of a metal oxide. As a result, it was confirmed that the obtained metal oxide was a supported copper-zinc catalyst in which the mass ratio of zinc to copper (zinc/copper) in the metal oxide was 0.25, and the content of copper in the catalyst was 36% by mass.

Production Example 8

The same procedure as in Production Example 1 was repeated except that 0.17 g of yttrium nitrate hexahydrate was used in place of 69 g of magnesium nitrate hexahydrate, and the calcination treatment was carried out at 600° C. under an air flow for 1 h, thereby obtaining a catalyst in the form of a metal oxide. As a result, it was confirmed that the obtained metal oxide was a supported copper-yttrium catalyst in which the mass ratio of a sum of magnesium and yttrium to copper [(magnesium+yttrium)/copper] in the metal oxide was 0.43, and the content of copper in the catalyst was 35% by mass.

Production Example 9

A separable flask was charged with 100 g of copper nitrate trihydrate and 10 g of calcium nitrate tetrahydrate. The contents of the flask were dissolved in 2 L of ion-exchanged water, and then heated while stirring. The flask was further charged at 50° C. with 33 g of synthesized zeolite ("ZEOLUM A-4" available from Tosoh Corporation.), and the contents of the flask were heated to 90° C. After dropping an aqueous sodium carbonate solution to the above obtained solution over 1 h to control a pH value thereof to 7, the resultant mixed solution was aged for 1 h. The thus obtained suspended solution was cooled and then filtered and washed with water, and further dried at 110° C. over a whole day and night. The obtained dried product was calcined at 600° C. under an air flow for 1 h, thereby obtaining a catalyst in the form of a metal oxide. As a result, it was confirmed that the mass ratio of calcium to copper (calcium/copper) in the thus obtained metal oxide was 0.06, and the content of copper in the catalyst was 39% by mass.

Example 1

A rotary autoclave was charged with 300 g of N,N-dimethyl lauroyl amide and 5% by mass of the catalyst produced in Production Example 1 (on the basis of the raw amide compound). An inside of the autoclave was purged with nitrogen, and then hydrogen was introduced thereinto until an inside pressure of the autoclave was increased to 1.5 MPaG. Thereafter, while maintaining the inside pressure of the autoclave at 1.5 MPaG, hydrogen was introduced into the reaction system at a rate of 40 L/h (1.4 mol/h per 1 mol of the raw amide compound). Next, the reaction system was heated to 230° C. at which the hydrogen-reduction reaction was carried out until no raw amide compound was detected therein as measured by gas chromatography. The reaction rate upon the above reaction was shown in Table 1. Meanwhile, the reaction rate was calculated from a hourly ratio of the amount of the amide compound reacted for six hours from initiation of the reaction as measured by gas chromatography to the whole amount of the raw amide compound charged [(amount (mol) of the amide compound reacted per 1 hour)/(whole amount (kg) of the raw amide compound charged)] (this definition is also applied to the subsequent Examples). Next, while maintaining the same reaction temperature and pressure as well as the same hydrogen introduction rate, dimethyl amine was additionally introduced to the reaction system at a rate of 2 to 1 L/h (from 0.07 to 0.03 mol/h per 1 mol of the raw amide compound), and the resultant mixture was reacted for 2 h. The thus obtained reaction product was subjected to filtration to remove the catalyst therefrom, and then the composition of the thus separated product solution was analyzed by gas chromatography. The results are shown in Table 1.

Example 2

The hydrogen-reduction reaction was conducted in the same manner as in Example 1 except for using the catalyst produced in Production Example 2 in place of the catalyst produced in Production Example 1 and changing the reaction temperature to 250° C. As a result, 9 hours after initiation of the reaction, the amount of the raw amide compound as measured by gas chromatography was reduced below the lower detection limit. The reaction rate upon the above reaction was shown in Table 1. Next, while maintaining the same reaction temperature and pressure as well as the same hydrogen introduction rate, dimethyl amine was additionally introduced to the reaction system at a rate of 1 to 0.4 L/h (from 0.03 to 0.01 mol/h per 1 mol of the raw amide compound), and the resultant mixture was reacted for 1 h. The thus obtained reaction product was subjected to filtration to remove the catalyst therefrom, and then the composition of the thus separated product solution was analyzed by gas chromatography. The results are shown in Table 1.

Example 3

The hydrogen-reduction reaction was conducted until the amount of the raw amide compound as measured by gas chromatography was reduced below the lower detection limit, in the same manner as in Example 2 except that the amount of the catalyst used was changed from 5% by mass to 3% by mass (on the basis of the raw amide compound). The reaction rate upon the above reaction was shown in Table 1. Next, while maintaining the same reaction temperature and pressure as well as the same hydrogen introduction rate, dimethyl amine was additionally introduced to the reaction system at a rate of 2 to 1 L/h (from 0.07 to 0.03 mol/h per 1 mol of the raw amide compound), and the resultant mixture was reacted for 3 h. The thus obtained reaction product was subjected to filtration to remove the catalyst therefrom, and then the composition of the thus separated product solution was analyzed by gas chromatography. The results are shown in Table 1.

Example 4

The hydrogen-reduction reaction was conducted until the amount of the raw amide compound as measured by gas chromatography was reduced below the lower detection limit, in the same manner as in Example 1 except for using the catalyst produced in Production Example 3 in place of the catalyst produced in Production Example 1 and maintaining the reaction temperature and pressure at 250° C. and 1.5 MPaG, respectively. The reaction rate upon the above reaction was shown in Table 1. Next, after changing the reaction temperature to 220° C. and the reaction pressure to normal pressures but while maintaining the same hydrogen introduction rate, dimethyl amine was additionally introduced to the reaction system at a rate of 3 to 2 L/h (from 0.10 to 0.07 mol/h per 1 mol of the raw amide compound), and the resultant mixture was reacted for 2 h. The thus obtained reaction product was subjected to filtration to remove the catalyst therefrom, and then the composition of the thus separated product solution was analyzed by gas chromatography. The results are shown in Table 1.

Example 5

The hydrogen-reduction reaction was conducted until the amount of the raw amide compound as measured by gas chromatography was reduced below the lower detection limit, in the same manner as in Example 4 except for using the catalyst produced in Production Example 4 in place of the catalyst produced in Production Example 4. The reaction rate upon the above reaction was shown in Table 1. Next, after changing the reaction pressure to 0.5 MPaG but while maintaining the same reaction temperature and hydrogen introduction rate, dimethyl amine was additionally introduced to the reaction system at a rate of 2 to 1 L/h (from 0.07 to 0.03 mol/h per 1 mol of the raw amide compound), and the resultant mixture was reacted for 3 h. The thus obtained reaction product was subjected to filtration to remove the catalyst therefrom, and then the composition of the thus separated product solution was analyzed by gas chromatography. The results are shown in Table 1.

Example 6

The hydrogen-reduction reaction was conducted until the amount of the raw amide compound as measured by gas chromatography was reduced below the lower detection limit, in the same manner as in Example 1 except for using the catalyst produced in Production Example 5 in place of the catalyst produced in Production Example 1 and maintaining the reaction temperature and pressure at 230° C. and 5.0 MPaG, respectively. The reaction rate upon the above reaction was shown in Table 1. Next, after changing the reaction pressure to 3.0 MPaG but while maintaining the same reaction temperature and hydrogen introduction rate, dimethyl amine was additionally introduced to the reaction system at a rate of 3 to 2 L/h (from 0.1 to 0.07 mol/h per 1 mol of the raw amide compound), and the resultant mixture was reacted for 3 h. The thus obtained reaction product was subjected to filtration to remove the catalyst therefrom, and then the composition of the thus separated product solution was analyzed by gas chromatography. The results are shown in Table 1.

Example 7

The hydrogen-reduction reaction was conducted until the amount of the raw amide compound as measured by gas chromatography was reduced below the lower detection limit, in the same manner as in Example 1 except for using the catalyst produced in Production Example 6 in place of the catalyst produced in Production Example 1 and maintaining the reaction temperature and pressure at 250° C. and 0.5 MPaG, respectively. The reaction rate upon the above reaction was shown in Table 1. Next, after changing the reaction temperature to 220° C. and the reaction pressure to normal pressures but while maintaining the same hydrogen introduction rate, dimethyl amine was additionally introduced to the reaction system at a rate of 3 to 2 L/h (from 0.10 to 0.07 mol/h per 1 mol of the raw amide compound), and the resultant mixture was reacted for 1 h. The thus obtained reaction product was subjected to filtration to remove the catalyst therefrom, and then the composition of the thus separated product solution was analyzed by gas chromatography. The results are shown in Table 1.

reaction product was subjected to filtration to remove the catalyst therefrom, and then the composition of the thus separated product solution was analyzed by gas chromatography. The results are shown in Table 2.

Comparative Example 1

A rotary autoclave was charged with 300 g of N,N-dimethyl lauroyl amide and 5% by mass of the catalyst produced in Production Example 7 (on the basis of the raw amide

TABLE 1

| | Catalyst | Reaction rate [×10$^{-2}$ mol/(kg·h)] | Introduction of dimethyl amine | Composition of reaction product (mass %) | | | |
|---|---|---|---|---|---|---|---|
| | | | | DMLA*[1] | LA*[2] | DLMA*[3] | others |
| Example 1 | Production Example 1 | 61.2 | BT*[4] | 86.4 | 9 | 3.1 | 1.5 |
| | | | AT*[5] | 94.5 | 0.3 | 3.7 | 1.5 |
| Example 2 | Production Example 2 | 63.7 | BT*[4] | 86.3 | 6.0 | 5.7 | 2.0 |
| | | | AT*[5] | 91.5 | 0.2 | 6.3 | 2.0 |
| Example 3 | Production Example 2 | 52.2 | BT*[4] | 86.1 | 8.3 | 3.5 | 2.1 |
| | | | AT*[5] | 93.3 | 0.4 | 4.2 | 2.1 |
| Example 4 | Production Example 3 | 53.6 | BT*[4] | 86.8 | 8.6 | 2.6 | 2.0 |
| | | | AT*[5] | 93.7 | 0.8 | 3.4 | 2.1 |
| Example 5 | Production Example 4 | 58.3 | BT*[4] | 84.4 | 8.0 | 4.5 | 3.1 |
| | | | AT*[5] | 91.3 | 0.7 | 4.9 | 3.1 |
| Example 6 | Production Example 5 | 38.4 | BT*[4] | 82.7 | 11.7 | 4.8 | 0.8 |
| | | | AT*[5] | 91.6 | 0.9 | 6.2 | 1.3 |
| Example 7 | Production Example 6 | 42.2 | BT*[4] | 85.4 | 6.9 | 3.9 | 3.8 |
| | | | AT*[5] | 91.1 | 0.6 | 4.4 | 3.9 |

Note
*[1] DMLA = Dimethyl lauryl amine;
*[2] LA = Laury alcohol;
*[3] DLMA = Dilauryl methyl amine;
*[4] BT = Before the treatment;
*[5] AT = After the treatment Example 8

The hydrogen-reduction reaction was conducted until the amount of the raw amide compound as measured by gas chromatography was reduced below the lower detection limit, in the same manner as in Example 1 except for using the catalyst produced in Production Example 7 in place of the catalyst produced in Production Example 1 and introducing hydrogen into the reaction system at a rate of 70 L/h (2.4 mol/h per 1 mol of the raw amide compound). The reaction rate upon the above reaction was shown in Table 2. Next, after changing the reaction temperature to 180° C. and the reaction pressure to 0.2 MPaG but while maintaining the same hydrogen introduction rate, dimethyl amine was additionally introduced to the reaction system at a rate of 2 to 1 L/h (from 0.07 to 0.03 mol/h per 1 mol of the raw amide compound), and the resultant mixture was reacted for 2 h. The thus obtained compound). An inside of the autoclave was purged with nitrogen, and then hydrogen was introduced thereinto until an inside pressure of the autoclave was increased to 1.5 MPaG. Thereafter, while maintaining the inside pressure of the autoclave at 1.5 MPaG, hydrogen and dimethyl amine were introduced into the reaction system at rates of 70 L/h (2.4 mol/h per 1 mol of the raw amide compound) and from 2 to 1 L/h (from 0.07 to 0.03 mol/h per 1 mol of the raw amide compound), respectively, and the resultant mixture was reacted. The thus obtained reaction product was subjected to filtration to remove the catalyst therefrom, and then the composition of the thus separated product solution was analyzed by gas chromatography. The results are shown in Table 2. Meanwhile, as a result of analyzing the composition of the reaction product, it was confirmed that the amount of dimethyl lauroyl amide was below the lower detection limit

TABLE 2

| | Catalyst | Reaction rate [×10$^{-2}$ mol/(kg·h)] | Introduction of dimethyl amine | Composition of reaction product (mass %) | | | |
|---|---|---|---|---|---|---|---|
| | | | | DMLA *[1] | LA *[2] | DLMA *[3] | others |
| Example 8 | Production Example 7 | 51.4 | BT *[4] | 85.1 | 7.4 | 4.9 | 2.6 |
| | | | AT *[5] | 91.5 | 0.5 | 5.4 | 2.6 |
| Comp. Example 1 | Production Example 7 | 36.4 | | 86.4 | 0.6 | 10.5 | 2.5 |

Note
*1: DMLA = Dimethyl lauryl amine;
*2: LA = Laury alcohol;
*3: DLMA = Dilauryl methyl amine;
*4: BT = Before the treatment;
*5: AT = After the treatment

Example 9

The hydrogen-reduction reaction was conducted until the amount of the raw amide compound as measured by gas chromatography was reduced below the lower detection limit, in the same manner as in Example 4 except for using the catalyst produced in Production Example 8 in place of the catalyst produced in Production Example 3. The reaction rate upon the above reaction was shown in Table 3. Next, after changing the reaction pressure to 0.2 MPaG but while maintaining the same reaction temperature and hydrogen introduction rate, dimethyl amine was additionally introduced to the reaction system at a rate of 3 to 2 L/h (from 0.10 to 0.07 mol/h per 1 mol of the raw amide compound), and the resultant mixture was reacted for 3 h. The thus obtained reaction product was subjected to filtration to remove the catalyst therefrom, and then the composition of the thus separated product solution was analyzed by gas chromatography. The results are shown in Table 3.

Example 10

The hydrogen-reduction reaction was conducted until the amount of the raw amide compound as measured by gas chromatography was reduced below the lower detection limit, in the same manner as in Example 4 except for using a commercially available Cu—Zn catalyst ("Cu0890p" available from N.E. Chemcat Corp.) in place of the catalyst produced in Production Example 3. The reaction rate upon the above reaction was shown in Table 3. Next, after changing the reaction pressure to normal pressures but while maintaining the same reaction temperature and hydrogen introduction rate, dimethyl amine was additionally introduced to the reaction system at a rate of 9 to 8 L/h (from 0.30 to 0.27 mol/h per 1 mol of the raw amide compound), and the resultant mixture was reacted for 3 h. The thus obtained reaction product was subjected to filtration to remove the catalyst therefrom, and the composition of the thus separated product solution was analyzed by gas chromatography. The results are shown in Table 3.

was subjected to filtration to remove the catalyst therefrom, and then the composition of the thus separated product solution was analyzed by gas chromatography. As a result, it was confirmed that the amount of dimethyl stearoyl amide contained in the reaction product was below the lower detection limit, and the reaction product was composed of 83.1% of dimethyl stearyl amine, 5.5% of distearyl methyl amine and 8.8% of stearyl alcohol. Further, the reaction rate upon the above reaction was 39.5 [$\times 10^{-2}$ mol/(kg·h)]. Next, after changing the reaction pressure to 0.2 MPaG but while maintaining the same reaction temperature and hydrogen introduction rate, dimethyl amine was additionally introduced to the reaction system at a rate of 2 to 1 L/h (from 0.07 to 0.03 mol/h per 1 mol of the raw amide compound), and the resultant mixture was reacted for 2 h. As a result, it was confirmed that the reaction product was composed of 90.4% of dimethyl stearyl amine, 5.6% of distearyl methyl amine and 0.8% of stearyl alcohol.

Comparative Example 2

The reaction was conducted in the same manner as in Comparative Example 1 except for using a commercially available Cu—Cr catalyst ("Cu1800p" available from N.E. Chemcat Corp.) in place of the catalyst produced in Production Example 7 and introducing hydrogen at a rate of 40 L/h (1.4 mol/h per 1 mol of the raw amide compound). The thus obtained reaction product was subjected to filtration to remove the catalyst therefrom, and then the composition of the thus separated product solution was analyzed by gas chromatography. As a result, it was confirmed that the amount of dimethyl lauroyl amide contained in the reaction product was below the lower detection limit, and the reaction product was composed of 82.9% of dimethyl lauryl amine, 12.4% of dilauryl methyl amine and 0.6% of lauryl alcohol. Further, the reaction rate upon the above reaction was 36.4 [$\times 10^{-2}$ mol/(kg·h)].

Comparative Example 3

The hydrogen-reduction reaction was conducted until the amount of the raw amide compound as measured by gas

TABLE 3

| | Catalyst | Reaction rate [$\times 10^{-2}$ mol/(kg·h)] | Introduction of dimethyl amine | Composition of reaction product (mass %) | | | |
|---|---|---|---|---|---|---|---|
| | | | | DMLA*[1] | LA*[2] | DLMA*[3] | others |
| Example 9 | Production Example 8 | 60.3 | BT*[4] | 85.5 | 6.6 | 5.7 | 2.2 |
| | | | AT*[5] | 90.6 | 0.9 | 5.9 | 2.6 |
| Example 10 | Commercially available catalyst | 67.6 | BT*[4] | 85.5 | 8.1 | 3.5 | 2.9 |
| | | | AT*[5] | 92.2 | 0.8 | 3.7 | 3.3 |

Note
*[1]DMLA = Dimethyl lauryl amine;
*[2]LA = Laury alcohol;
*[3]DLMA = Dilauryl methyl amine;
*[4]BT = Before the treatment;
*[5]AT = After the treatment

Example 11

The hydrogen-reduction reaction was conducted until the amount of the raw amide compound as measured by gas chromatography was reduced below the lower detection limit, in the same manner as in Example 4 except for using 300 g of N,N-dimethyl stearoyl amide in place of 300 g of N,N-dimethyl lauroyl amide and using the catalyst produced in Production Example 9 in place of the catalyst produced in Production Example 3. The thus obtained reaction product chromatography was reduced below the lower detection limit, in the same manner as in Example 10 except for using a commercially available Cu—Cr catalyst ("Cu1800p" available from N.E. Chemcat Corp.) in place of the commercially available Cu—Zn catalyst. The thus obtained reaction product was subjected to filtration to remove the catalyst therefrom, and then the composition of the thus separated product solution was analyzed by gas chromatography. As a result, it was confirmed that the amount of dimethyl lauroyl amide contained in the reaction product was below the lower detection limit, and the reaction product was composed of 79.8% of dimethyl lauryl amine, 9.4% of dilauryl methyl amine and 5.3% of lauryl alcohol. Further, the reaction rate upon the above reaction was 45.1 [×10$^{-2}$ mol/(kg·h)]. Next, after changing the reaction pressure to normal pressures but while maintaining the same reaction temperature and hydrogen introduction rate, dimethyl amine was additionally introduced to the reaction system at a rate of 9 to 8 L/h (from 0.30 to 0.27 mol/h per 1 mol of the raw amide compound), and the resultant mixture was reacted for 1 h. As a result, it was confirmed that the reaction product was composed of 84.4% of dimethyl lauryl amine, 9.6% of dilauryl methyl amine and 0.8% of lauryl alcohol.

Example 12

The reaction product obtained in Example 1 was subjected to purification and fractionation procedure by distillation, thereby obtaining lauryl dimethyl amine (purity as measured by gas chromatography: 99.9%). A 1 L four-necked flask equipped with a thermometer, a stirrer, a cooling tube and a chopping funnel was charged with 259 g of the thus obtained lauryl dimethyl amine (weight-average molecular weight: 215.7) and 440 g of ion-exchanged water, and the contents of the flask were heated to 90° C. Thereafter, 92 g of a 45% hydrogen peroxide aqueous solution was dropped into the flask over 1 h. Further, the contents of the flask were stirred at 90° C. for 8 h, thereby obtaining a reaction product containing about 35% of lauryl dimethyl amine oxide. The hue and odor of the thus obtained product were evaluated immediately after production thereof and after preserving the product at 60° C. The results are shown in Table 4.

Example 13

The same procedure as in Example 12 was repeated except for using the reaction product obtained in Example 3 in place of the reaction product obtained in Example 1, thereby obtaining a reaction product containing lauryl dim ethyl amine oxide. The hue and odor of the thus obtained product were evaluated immediately after production thereof and after preserving the product at 60° C. The results are shown in Table 4.

Comparative Example 4

The same procedure as in Example 12 was repeated except for using the reaction product obtained in Comparative Example 3 in place of the reaction product obtained in Example 1, thereby obtaining a reaction product containing lauryl dimethyl amine oxide as aimed. The hue and odor of the thus obtained product were evaluated immediately after production thereof and after preserving the product at 60° C. The results are shown in Table 4.

Meanwhile, the hue and odor of the respective reaction products were evaluated by the following methods.
(Evaluation of Hue)
The sample was placed in a glass container for measurement to measure a hue thereof using a tintometer "Lovibond Tintometer PFX995".
(Evaluation of Odor)
The sample was subjected to sensory test by expert panelists to evaluate an odor thereof according to the following 4 ratings A, B, C and D.
Evaluation Criteria
A: Excellent
B: Good
C: Slightly poor
D: Poor

TABLE 4

|  | Amine product | Hue (APHA) | | | Odor | |
| --- | --- | --- | --- | --- | --- | --- |
|  |  | IA *1 | After 3 days | After 6 days | IA *1 | After 3 days |
| Example 12 | Example 1 | 5 | 30 | 250 to 300 | A | B |
| Example 13 | Example 3 | 5 | 30 | 300 to 400 | A | B |
| Comp. Example 4 | Comp. Example 3 | 10 | 50 | >500 | A | C |

Note
*1: IA = Immediately after production

Meanwhile, in the above Examples, etc., the contents of the respective metal atoms were measured by the above ICP emission spectrometry using an analyzer "JY238" available from Jobin Ybon Inc.

Also, the analysis of composition of the respective reaction products by gas chromatography was carried out using the following apparatus.

Gas Chromatograph: "HEWLETT PACKARD Series 6890"

Column: "DB-17" available from J & W Inc. (inner diameter×length×film thickness: 15 m×0.25 m×0.5 μm)

The invention claimed is:

1. A process for producing a tertiary amine represented by formula (2):

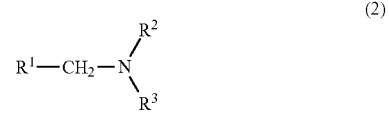

(2)

wherein R$^1$ is a linear or branched aliphatic hydrocarbon group having 5 to 23 carbon atoms; and R$^2$ and R$^3$ are respectively a linear or branched alkyl group having 1 to 6 carbon atoms and may be the same or different,
in the presence of a chromium-free catalyst comprising copper and at least one element selected from the group consisting of magnesium, calcium, barium, manganese, and yttrium, said process comprising:
(a) reducing an amide compound represented by formula (1):

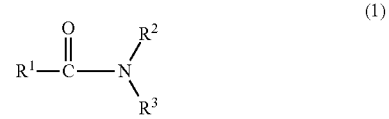

(1)

wherein R$^1$, R$^2$ and R$^3$ are the same as defined above,
in a hydrogen atmosphere, to obtain a reaction product; and
(b) reacting a dialkyl amine having a linear or branched alkyl group having 1 to 6 carbon atoms with said reaction product.

2. A process according to claim 1, wherein said chromium-free catalyst comprises at least one element selected from the group consisting of magnesium, calcium, barium, and manganese.

3. A process according to claim 1, wherein said chromium-free catalyst comprises copper in an amount from 5 to 70% by mass in terms of metallic copper.

4. A process according to claim 1, wherein a mass ratio of a content of the at least one element selected from the group consisting of magnesium, calcium, barium, manganese, and yttrium to the content of the copper in said chromium-free catalyst is from 0.01 to 20.

5. A process according to claim 1, wherein in said reducing and said reacting, hydrogen is flowed through the reaction mixture at a rate of from 0.1 to 15 mol/h per 1 mol of the starting amount of amide compound.

6. A process according to claim 1, wherein in said reacting, said dialkyl amine having a linear or branched alkyl group having 1 to 6 carbon atoms is introduced into said reaction product at a rate of from 0.001 to 1 mol/h per 1 mol of the starting amount of amide compound.

7. A process according to claim 1, wherein the catalyst is present in an amount of from 0.01 to 20% by mass on the basis of the amide compound represented by formula (1).

8. A process for producing an amine oxide, comprising:
(1) preparing a tertiary amine by a process according to claims 1; and
(2) reacting said tertiary amine with hydrogen peroxide.

9. A process according to claim 1, wherein said (b) reacting is commenced after the amount of said amide represented by formula (1) has been reduced to 5% by mass or less.

10. A process according to claim 1, wherein said (b) reacting is commenced after the amount of said amide represented by formula (1) has been reduced to 1% by mass or less.

11. A process according to claim 1, which comprises:
(i) forming a mixture comprising said amide represented by formula (1) and said chromium-free catalyst in a reaction vessel;
(ii) introducing hydrogen into said reaction vessel;
(iii) reacting said amide represented by formula (1) with said hydrogen until the amount of amide represented by formula (1) has been reduced to 5% by mass less, to obtain a reaction product; and
(iv) reacting said reaction product with said dialkyl amine having a linear or branched alkyl group having 1 to 6 carbon atoms.

12. A process according to claim 1, which comprises:
(i) forming a mixture comprising said amide represented by formula (1) and said chromium-free catalyst in a reaction vessel;
(ii) introducing hydrogen into said reaction vessel;
(iii) reacting said amide represented by formula (1) with said hydrogen until the amount of amide represented by formula (1) has been reduced to 1% by mass less, to obtain a reaction product; and
(iv) reacting said reaction product with said dialkyl amine having a linear or branched alkyl group having 1 to 6 carbon atoms.

13. A process for producing an amine oxide, comprising:
(1) preparing a tertiary amine by a process according to claims 2; and
(2) reacting said tertiary amine with hydrogen peroxide.

14. A process for producing an amine oxide, comprising:
(1) preparing a tertiary amine by a process according to claims 3; and
(2) reacting said tertiary amine with hydrogen peroxide.

15. A process for producing an amine oxide, comprising:
(1) preparing a tertiary amine by a process according to claims 4; and
(2) reacting said tertiary amine with hydrogen peroxide.

16. A process for producing an amine oxide, comprising:
(1) preparing a tertiary amine by a process according to claims 5; and
(2) reacting said tertiary amine with hydrogen peroxide.

17. A process for producing an amine oxide, comprising:
(1) preparing a tertiary amine by a process according to claims 6; and
(2) reacting said tertiary amine with hydrogen peroxide.

18. A process for producing an amine oxide, comprising:
(1) preparing a tertiary amine by a process according to claims 7; and
(2) reacting said tertiary amine with hydrogen peroxide.

19. A process for producing an amine oxide, comprising:
(1) preparing a tertiary amine by a process according to claims 9; and
(2) reacting said tertiary amine with hydrogen peroxide.

20. A process for producing an amine oxide, comprising:
(1) preparing a tertiary amine by a process according to claims 10; and
(2) reacting said tertiary amine with hydrogen peroxide.

21. A process for producing an amine oxide, comprising:
(1) preparing a tertiary amine by a process according to claims 11; and
(2) reacting said tertiary amine with hydrogen peroxide.

22. A process for producing an amine oxide, comprising:
(1) preparing a tertiary amine by a process according to claims 12; and
(2) reacting said tertiary amine with hydrogen peroxide.

* * * * *